US009345897B2

(12) United States Patent
Dorman et al.

(10) Patent No.: US 9,345,897 B2
(45) Date of Patent: May 24, 2016

(54) MULTI-LAYER COVERING FOR CONTROL MODULES OF ELECTRICAL IMPLANTABLE MEDICAL DEVICES AND METHODS OF MAKING AND USING

(71) Applicant: BOSTON SCIENTIFIC NEUROMODULATION CORPORATION, Valencia, CA (US)

(72) Inventors: David M. Dorman, Castaic, CA (US); Benjamin Philip Hahn, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/622,264

(22) Filed: Feb. 13, 2015

(65) Prior Publication Data
US 2015/0238770 A1    Aug. 27, 2015

Related U.S. Application Data

(60) Provisional application No. 61/942,886, filed on Feb. 21, 2014.

(51) Int. Cl.
*A61N 1/00* (2006.01)
*A61N 1/375* (2006.01)
*A61N 1/36* (2006.01)

(52) U.S. Cl.
CPC ............. *A61N 1/3758* (2013.01); *A61N 1/3605* (2013.01); *A61N 1/3752* (2013.01); *A61N 1/3756* (2013.01)

(58) Field of Classification Search
CPC . A61N 1/3758; A61N 1/3605; A61N 1/3752; A61N 1/3756; A61N 1/375
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |
| 2008/0033500 A1* | 2/2008 | Strother ................. A61N 1/375 607/36 |

(Continued)

*Primary Examiner* — Robert N Wieland
(74) *Attorney, Agent, or Firm* — Lowe Graham Jones PLLC; Bruce E. Black

(57) ABSTRACT

A control module for an electrical stimulation system includes an electronic subassembly and a connector assembly coupled to the electronic subassembly. The connector assembly defines a port suitable for receiving a proximal end portion of an electrical stimulation lead. The connector assembly includes connector contacts coupled to the electronic subassembly and open to the port. The connector contacts are suitable for coupling to terminals disposed along the proximal end portion of the electrical stimulation lead when the electrical stimulation lead is received by the port. A covering is conformably disposed over the electronic subassembly and the connector assembly. The covering has an inner surface, an outer surface, and multiple layers.

19 Claims, 10 Drawing Sheets

(56) References Cited

U.S. PATENT DOCUMENTS

2010/0228348 A1* 9/2010 McClain ............... A61L 27/34
623/11.11
2012/0303105 A1* 11/2012 Askarinya ............. A61N 1/375
607/116
2013/0085350 A1* 4/2013 Schugt ................. A61B 5/686
600/302
2014/0273824 A1* 9/2014 Fenner ................ H04B 5/0031
455/41.1

* cited by examiner

MULTI-LAYER COVERING FOR CONTROL MODULES OF ELECTRICAL IMPLANTABLE MEDICAL DEVICES AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/942,886, filed Feb. 21, 2014, which is incorporated herein by reference.

FIELD

The present invention is directed to the area of implantable electrical medical device systems and methods of making and using the systems. The present invention is also directed to implantable electrical medical device systems having control modules with multi-layer coverings, as well as methods of making and using the control modules, coverings, and implantable electrical medical device systems.

BACKGROUND

Implantable electrical medical device systems, such as electrical stimulation systems, have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Implantable electrical stimulation systems can also be used for providing other types of stimulation including, for example, deep brain stimulation. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

Implantable electrical medical device systems can further be used for modulating cardio rhythm. For example, implantable electrical medical systems may be useful for regulating a heart beat via a pacemaker, sensing propagation of electrical signals, determining position and orientation of a device, or the like.

BRIEF SUMMARY

In one embodiment, a control module for an electrical stimulation system includes an electronic subassembly and a connector assembly coupled to the electronic subassembly. The connector assembly defines a port suitable for receiving a proximal end portion of an electrical stimulation lead. The connector assembly includes connector contacts coupled to the electronic subassembly and open to the port. The connector contacts are suitable for coupling to terminals disposed along the proximal end portion of the electrical stimulation lead when the electrical stimulation lead is received by the port. A covering is conformably disposed over the electronic subassembly and the connector assembly. The covering has an inner surface, an outer surface, and multiple layers.

In another embodiment, an implantable electrical stimulation system includes the control module described above, and at least one lead suitable for insertion into the connector assembly of the control module. The at least one lead includes at least one lead body having a distal end portion, a proximal end portion, and a longitudinal length; electrodes disposed along the distal end portion of the at least one lead body; terminals disposed along the proximal end portion of the at least one lead body; and conductors electrically coupling the terminals to the electrodes.

In yet another embodiment, a method of forming a control module of an implantable medical device includes forming a control-module assembly by coupling a connector assembly to an electronic subassembly. A covering is conformably disposed over the control-module assembly. The covering includes multiple layers.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical medical device systems and methods of making and using the systems. The present invention is also directed to implantable electrical medical device systems having control modules with multi-layer coverings, as well as methods of making and using the control modules, coverings, and implantable electrical medical device systems.

Suitable implantable electrical stimulation systems include, but are not limited to, a least one lead with one or more electrodes disposed along a distal end portion of the lead and one or more terminals disposed along the one or more proximal end portions of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
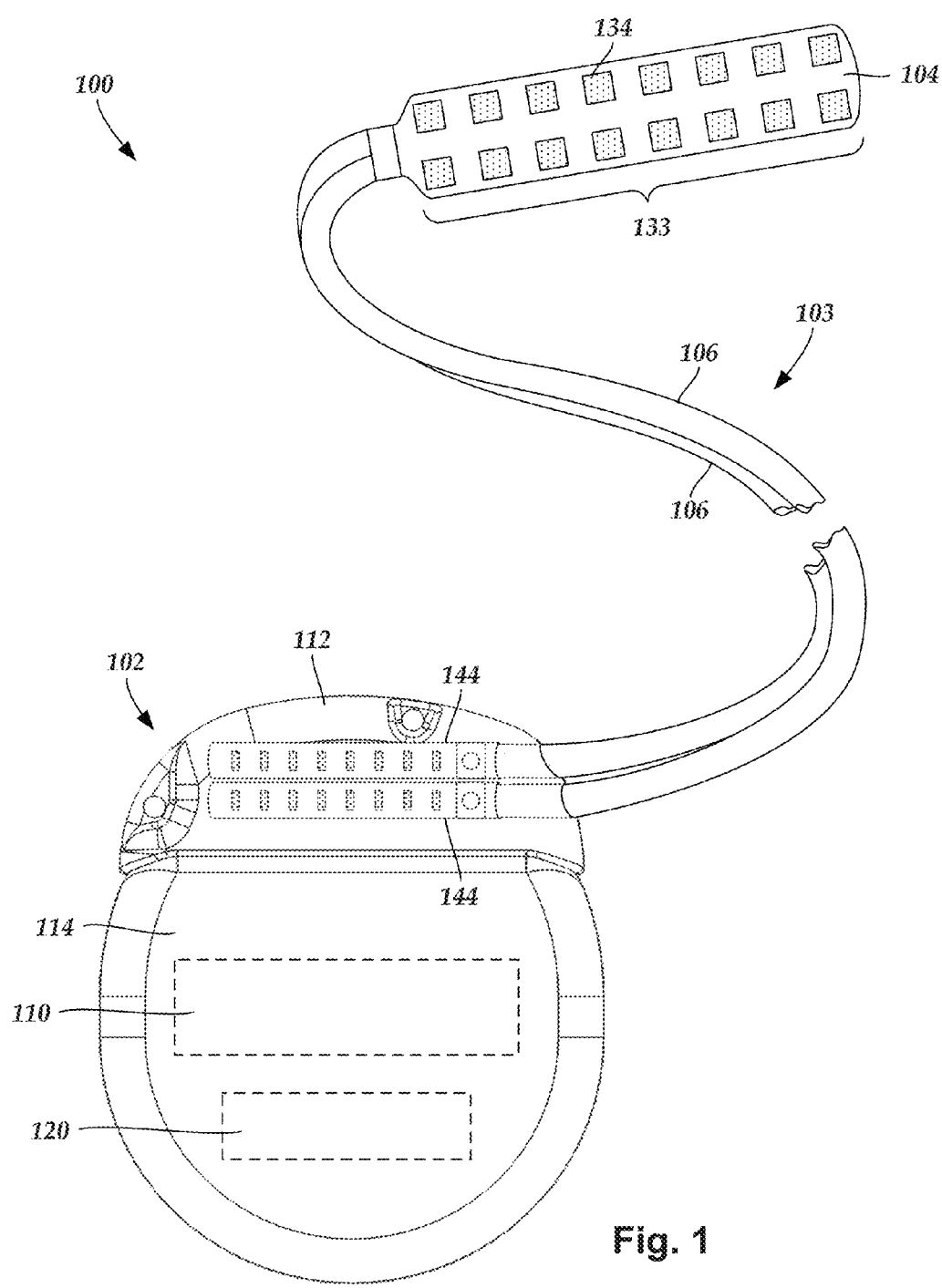
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106. In at least some embodiments, the number of electrodes in the array 133 is equal to the number of terminals.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
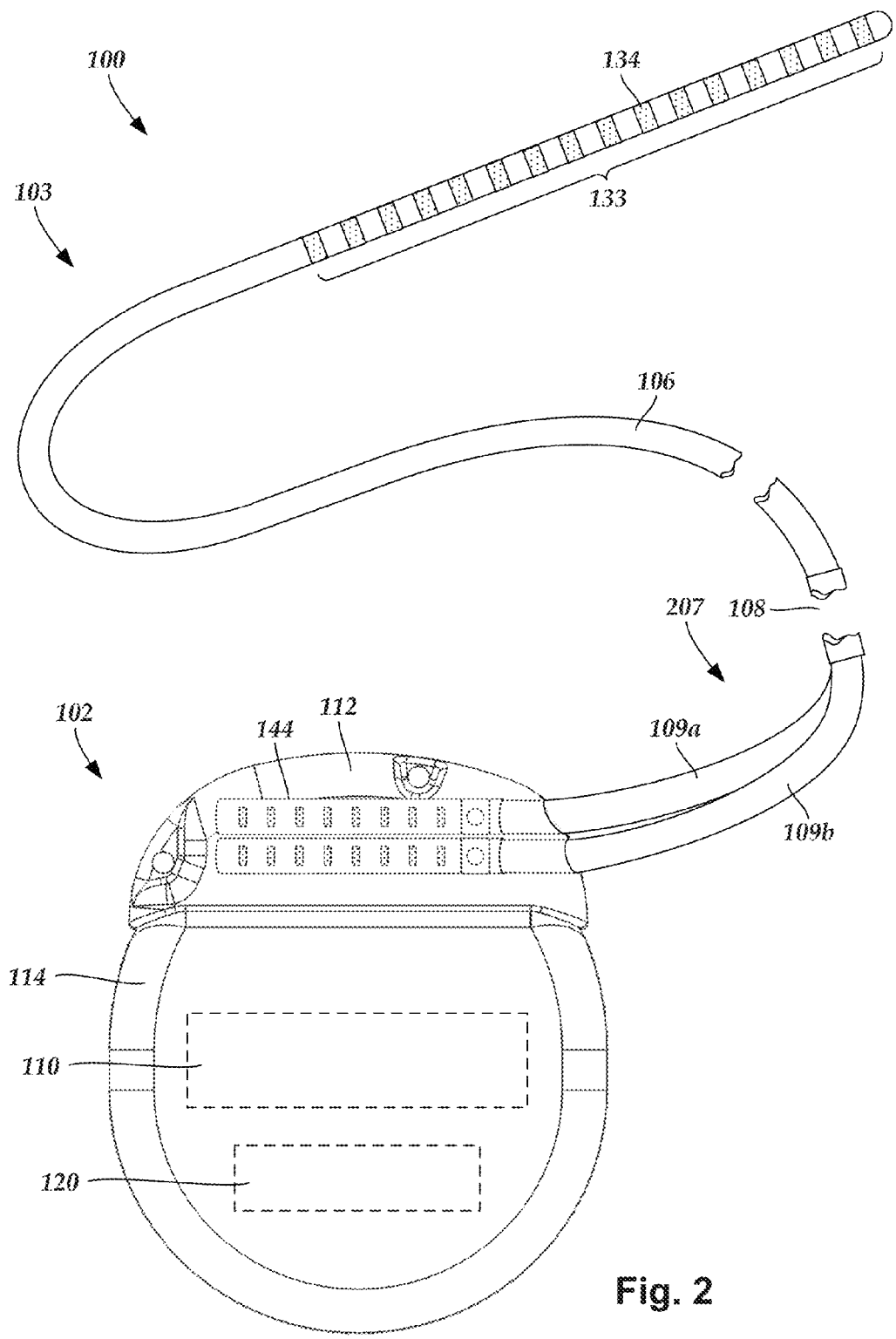
FIG. 2 is a schematic view of another embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along a distal end portion of the lead body 106. It will be understood that the lead of FIG. 2 can have multiple lead bodies. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 coupled to a sealed electronics housing 114. An electronic subassembly 110 and an optional power source 120 are disposed in the electronics housing 114. A connector assembly 144 is disposed in the connector housing 112. The connector assembly 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently, or detachably, coupled together.

Figure 3A:
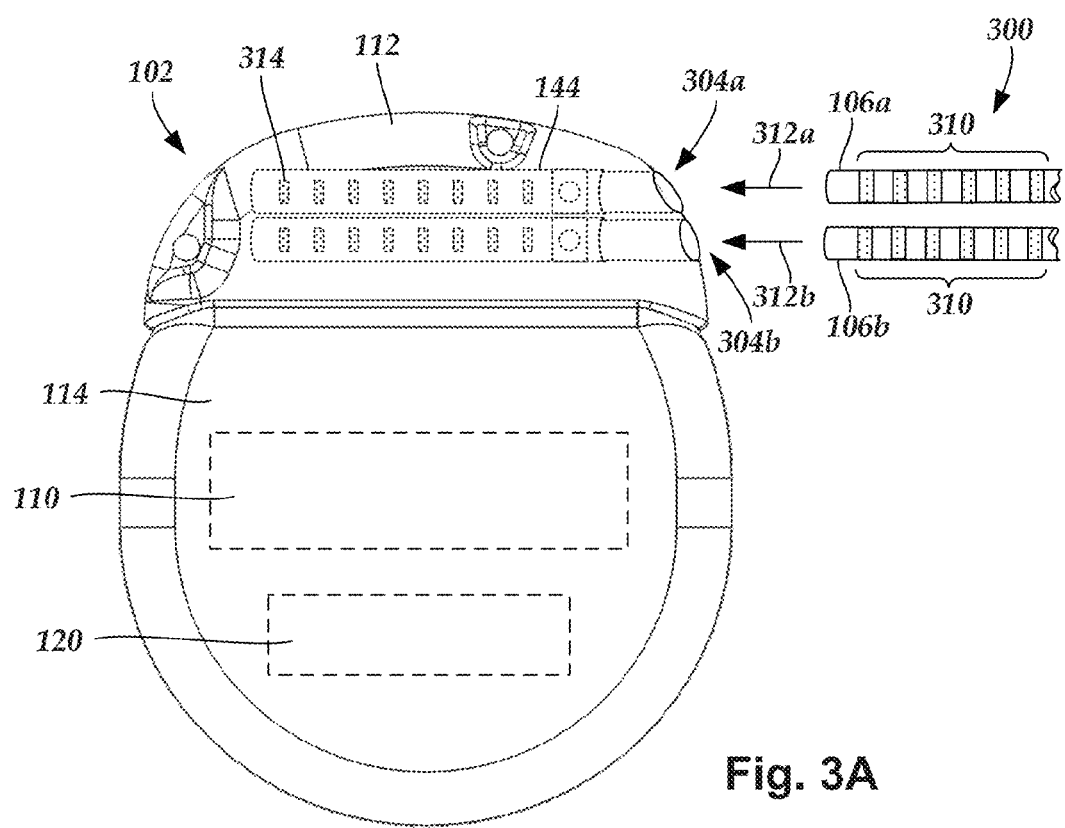
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the connector assembly 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The connector assembly 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The connector assembly 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
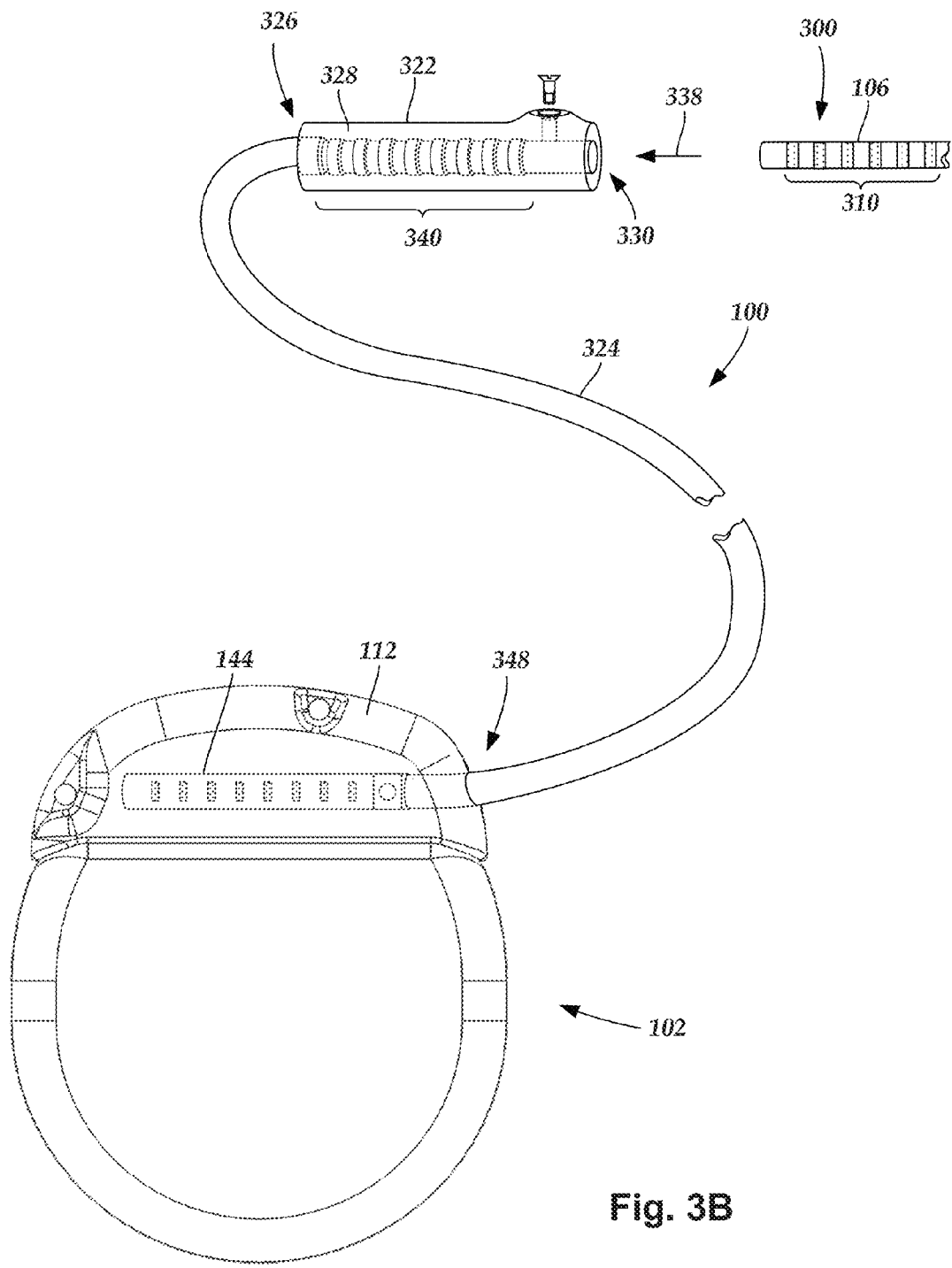
FIG. 3B is a schematic view of one embodiment of a lead extension configured and arranged to electrically couple the elongated device of FIG. 2 to the control module of FIG. 1, according to the invention.

FIG. 3B illustrates another embodiment of the electrical stimulation system 100. In FIG. 3B, the electrical stimulation system 100 includes a lead extension 324 that is configured and arranged to couple one or more elongated devices 300 (e.g., one of the lead bodies, a splitter, an adaptor, another lead extension, or the like or combinations thereof) to the control module 102. In FIG. 3B, the lead extension 324 is shown coupled to a single port 304 defined in the connector assembly 144. Additionally, the lead extension 324 is shown configured and arranged to couple to a single elongated device 300. In alternate embodiments, the lead extension 324 is configured and arranged to couple to multiple ports 304 defined in the connector assembly 144, or to receive multiple elongated devices 300, or both.

A lead extension connector 322 is disposed on the lead extension 324. In FIG. 3B, the lead extension connector 322 is shown disposed along a distal end portion 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, a proximal end portion 348 of the lead extension 324, opposite to the distal end portion 326, is similarly configured and arranged as a proximal end portion of the lead 103 (or other elongated device 300). The lead extension 324 may include a plurality of electrically conductive wires (not shown) that electrically couple the connector contacts 340 to the proximal end portion 348 of the lead extension 324 that is opposite to the distal end 326. In at least some embodiments, the conductive wires disposed in the lead extension 324 can be electrically coupled to a plurality of terminals (not shown) disposed along the proximal end portion 348 of the lead extension 324. In at least some embodiments, the proximal end portion 348 of the lead extension 324 is configured and arranged for insertion into a connector disposed in another lead extension (or another intermediate device). In other embodiments (and as shown in FIG. 3B), the proximal end portion 348 of the lead extension 324 is configured and arranged for insertion into the connector assembly 144.

Figure 4:
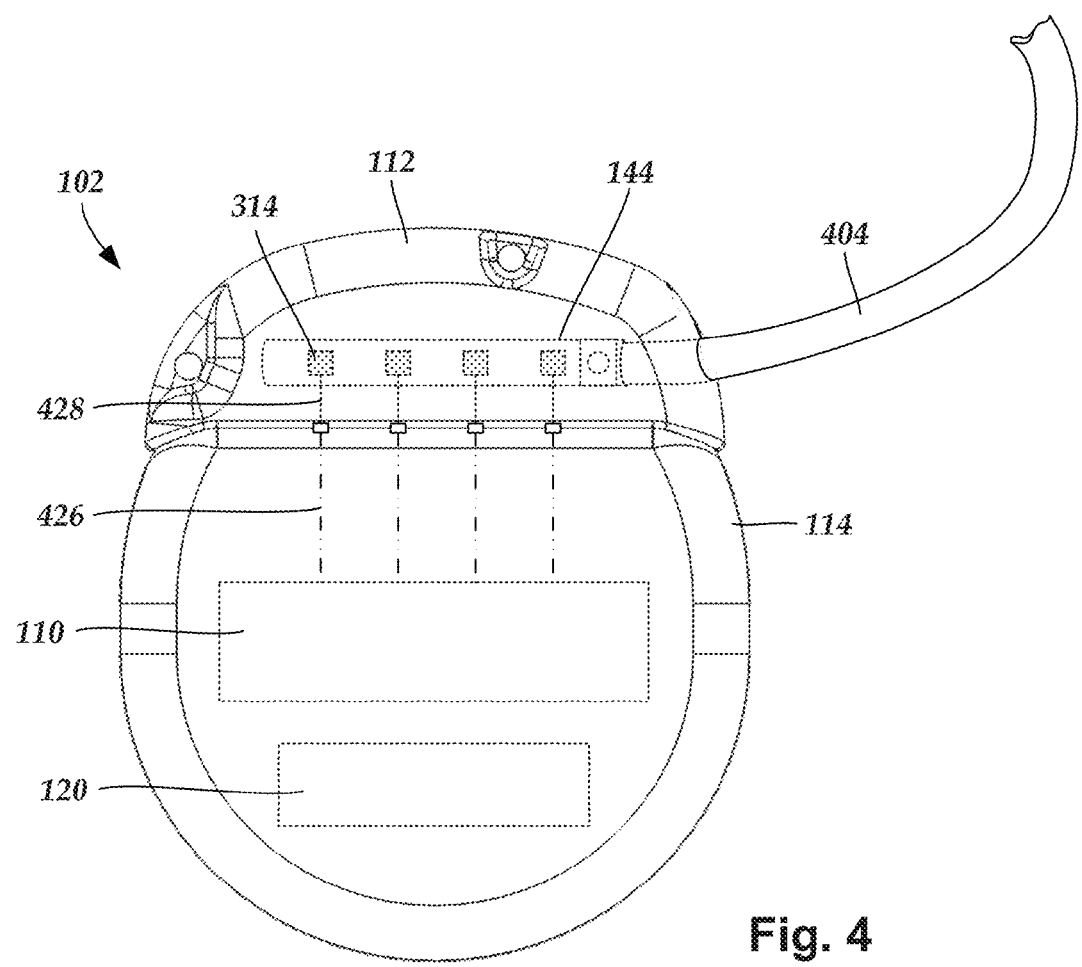
FIG. 4 is a schematic view of one embodiment of electrical pathways of a control module coupling a lead inserted into a connector housing of the control module of FIG. 1 to an electronic subassembly disposed in the control module, according to the invention.

Turning to FIG. 4, in at least some embodiments the connector contacts of the connector assembly are electrically coupled to the electronic subassembly within the sealed electronics housing via one or more feedthroughs. FIG. 4 illustrates, in a schematic side view, one embodiment of the control module 102. The control module 102 includes the connector housing 112 coupled to the sealed electronics housing 114. The connector assembly 144 is disposed in the connector housing 112. The electronic subassembly 110 and the optional power source 120 are disposed in the sealed electronics housing 114.

Connector contacts 314 are disposed in the connector assembly 144 and are configured and arranged for coupling with terminals disposed along an elongated device, such as a lead 404, when the lead 404 is disposed in the connector assembly 144. In FIG. 4, the connector assembly 144 is shown having four connector contacts 314. It will be understood that any suitable number of connector contacts 314 may be disposed in the connector housing 112 including, for example, one, two, three, four, five, six, seven, eight, nine, ten, eleven, twelve, fourteen, sixteen, twenty, twenty-four, thirty-two, or more connector contacts 314.

The connector contacts 314 are electrically coupled to the electronic subassembly 110 via feedthroughs 426 that extend through the sealed electronics housing 114 and that couple to the electronic subassembly 110. Optionally, the connector assembly 144 includes contact conductors, such as contact conductor 428, which couple the connector contacts 314 to portions of the feedthroughs 426 that extend outwardly from the sealed electronics housing 114. The contact conductors 428 can be formed from any suitable electrical conductor including, for example, single filar or multi-filar conductive wire.

Figure 5:
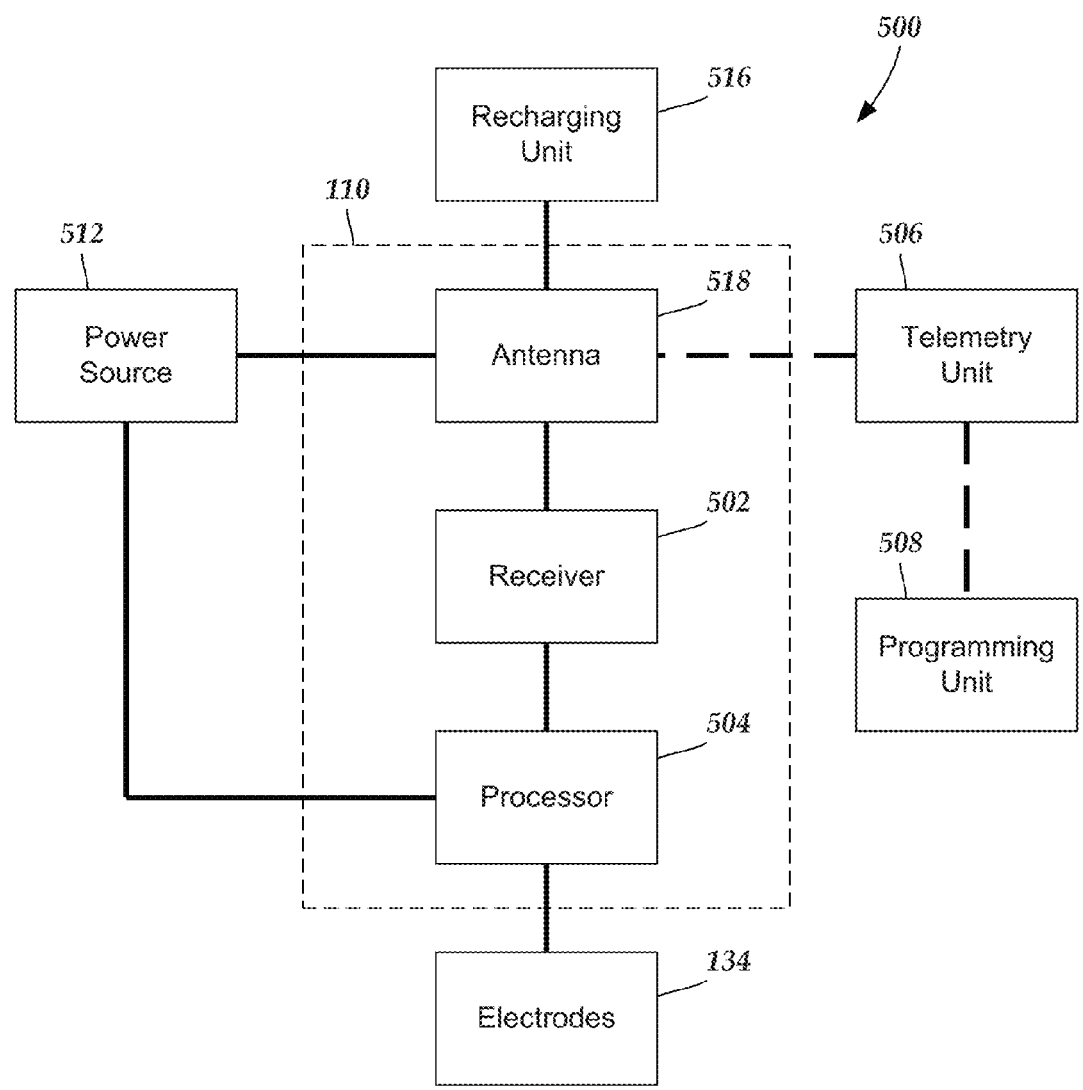
FIG. 5 is a schematic overview of one embodiment of electrical components of the control module of FIG. 4, including components of an electronic subassembly disposed in the control module of FIG. 4, according to the invention.

FIG. 5 is a schematic overview of one embodiment of components of an electrical stimulation system 500, including the electronic subassembly disposed within the sealed electronics housing of the control module. It will be understood that the electrical stimulation system can include more, fewer, or different components and can have a variety of different configurations including those configurations disclosed in the stimulator references cited herein.

Some of the components (for example, a power source 512, an antenna 518, a receiver 502, and a processor 504) of the electrical stimulation system can be positioned on one or more circuit boards or similar carriers within the sealed electronic housing, or implantable pulse generator, if desired. Any power source 512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 518 or a secondary antenna. The external power source can be in a device that is mounted on the skin of the user or in a unit that is provided near the user on a permanent or periodic basis.

If the power source 512 is a rechargeable battery, the battery may be recharged using the optional antenna 518, if desired. Power can be provided to the battery for recharging by inductively coupling the battery through the antenna to a recharging unit 516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 504 is generally included to control the timing and electrical characteristics of the electrical stimulation system. For example, the processor 504 can, if desired, control one or more of the timing, frequency, strength, duration, and waveform of the pulses. In addition, the processor 504 can select which electrodes can be used to provide stimulation, if desired. In some embodiments, the processor 504 selects which electrode(s) are cathodes and which electrode(s) are anodes. In some embodiments, the processor 504 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 508 that, for example, allows modification of pulse characteristics. In the illustrated embodiment, the processor 504 is coupled to a receiver 502 that, in turn, is coupled to the optional antenna 518. This allows the processor 504 to receive instructions from an external source to, for example, direct the pulse characteristics and the selection of electrodes, if desired.

In one embodiment, the antenna 518 is capable of receiving signals (e.g., RF signals) from an external telemetry unit 506 that is programmed by the programming unit 508. The programming unit 508 can be external to, or part of, the telemetry unit 506. The telemetry unit 506 can be a device that is worn on the skin of the user or can be carried by the user and can have a form similar to a pager, cellular phone, or remote control, if desired. As another alternative, the telemetry unit 506 may not be worn or carried by the user but may only be available at a home station or at a clinician's office. The programming unit 508 can be any unit that can provide information to the telemetry unit 506 for transmission to the electrical stimulation system 500. The programming unit 508 can be part of the telemetry unit 506 or can provide signals or information to the telemetry unit 506 via a wireless or wired connection. One example of a suitable programming unit is a computer operated by the user or clinician to send signals to the telemetry unit 506.

The signals sent to the processor 504 via the antenna 518 and the receiver 502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 500 to cease operation, to start operation, to start charging the battery, or to stop charging the battery. In other embodiments, the stimulation system does not include the antenna 518 or receiver 502 and the processor 504 operates as programmed.

Optionally, the electrical stimulation system 500 may include a transmitter (not shown) coupled to the processor 504 and the antenna 518 for transmitting signals back to the telemetry unit 506 or another unit capable of receiving the signals. For example, the electrical stimulation system 500 may transmit signals indicating whether the electrical stimulation system 500 is operating properly or not, or indicating when the battery needs to be charged, or the level of charge remaining in the battery, or the like. The processor 504 may also be capable of transmitting information about the pulse characteristics so that a user or clinician can determine or verify the characteristics.

Figure 6:
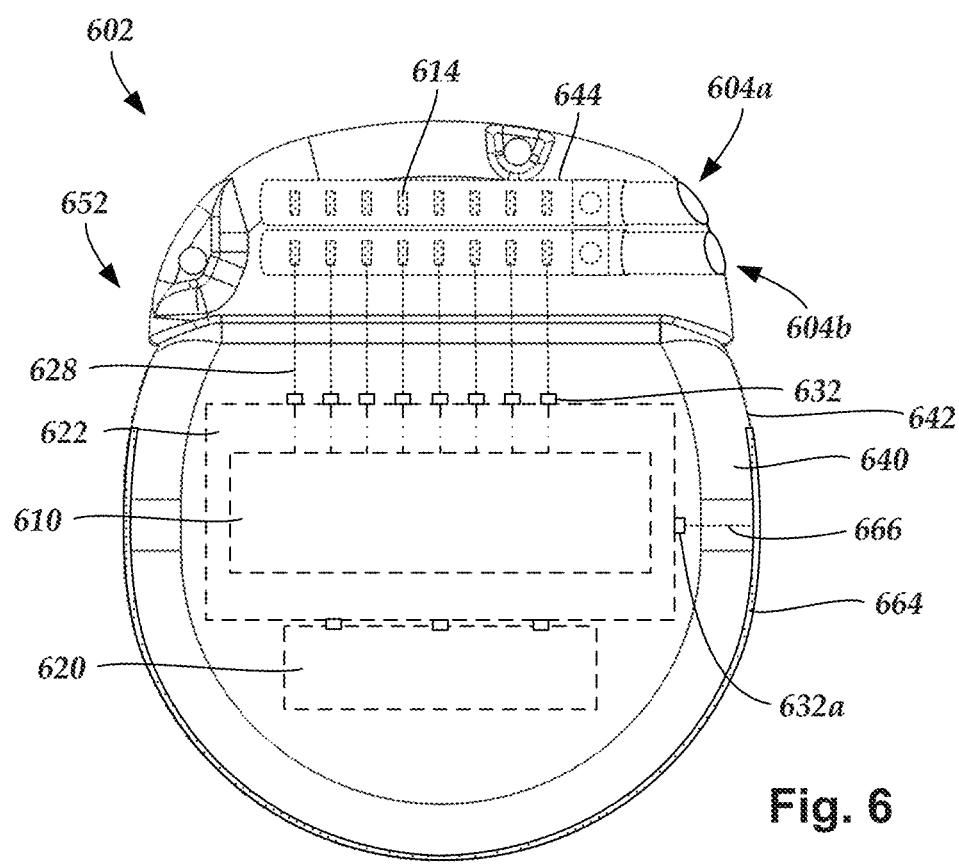
FIG. 6 is a schematic front view of one embodiment of a covering disposed over the control module of FIG. 4, the control module including a return electrode disposed along an outer surface of the covering, according to the invention.

Turning to FIG. 6, control modules are implantable into patients at a variety of different locations. The control modules can be implanted for a variety of different lengths of time including, for example, at least one week, one month, six months, one year, five years, ten years, twenty years, or longer.

Designing control modules to adequately withstand the harsh environments within which control modules are disposed, while at the same time reducing physical sizes and associated costs of building the control modules, has proven challenging. At least some conventional control modules contain electronics disposed within hermetically sealed metallic housings. Providing hermetically sealed metallic housings can be time-consuming and expensive. For example, such housings typically need to be welded together and be rigorously tested for leakage.

Anther time-consuming and expensive manufacturing step associated with fabricating conventional control-module housings includes attachment of the connector assembly to the electronic subassembly disposed in the hermetically sealed metallic housing. Connector assemblies are contained within connector housings. Connector housings are typically manufactured separately from the hermetically sealed metallic electronic housings and subsequently attached to outer surfaces of the sealed electronic housings. The connector contacts of the connector assemblies are typically coupled to feedthroughs that extend through the sealed electronic housings and couple to the electronic subassembly disposed within the hermetically sealed metallic housing. Formation of the feedthroughs and the coupling of the connector contacts to the electronic subassembly via the feedthroughs can be time-consuming and expensive.

As herein described, a control module for an implantable electronic medical device includes a multi-layer covering ("covering") disposed over the electronic subassembly and the connector assembly of the control module. At least one layer of the covering is formed from a polymer. In at least some embodiments, the covering is conformably disposed over the electronic subassembly and the connector assembly. In at least some embodiments, the covering is in intimate contact with the electronic subassembly and the connector assembly. In at least some embodiments, the covering is disposed directly over the electronic subassembly and the connector assembly. In at least some embodiments, one or more layers of the covering are formed by molding.

In at least some embodiments, the control module does not include a hermetically sealed metallic housing surrounding the electronic subassembly. In at least some embodiments, the control module does not include feedthroughs that extend through hermetically sealed metallic housings and that couple the connector assembly to the electronic subassembly.

Fabricating control modules without sealed metallic electronic housings surrounding the electronic subassembly may have many advantages. Fabricating control modules without sealed metallic electronic housings removes the manufacturing steps of welding together the metallic electronic housings, as well as performing corresponding tests for leakage, as well as making connections between feedthroughs and the electronic subassembly and between feedthroughs and the connector assembly.

Additionally, eliminating the sealed metallic electronic housing may cause a reduction in eddy currents, thereby improving the telemetry range created by the control module. Moreover, in embodiments that wirelessly recharge an optional power source disposed in the housing, eliminating the sealed metallic electronic housing may reduce the amount of time needed to recharge the power-source, and also reduce undesired heating occurring during recharging.

Providing a control module with the connector assembly and the electronic subassembly disposed in a multi-layer covering may enable the connector assembly and the electronic subassembly to be housed together in a single covering. In at least some embodiments, the covering enables the removal of feedthroughs extending through a hermetically sealed barrier. In at least some embodiments, the connector assembly can be mounted directly to the electronic subassembly. The size, or the shape, or both, of the control module may also be more easily altered with a covering than with a sealed metallic electronic housing.

The invention is described herein using a control module for a spinal cord stimulation system for clarity of illustration, and is not intended to be limiting. It will be understood that the disclosed control module, as well as the disclosed techniques for fabricating the control module, apply to any control module suitable for use with an implantable electronic medical device including, for example, deep brain stimulation systems, cardiac pacing systems, electrical sensing systems, position and orientation systems, or the like.

FIG. 6 illustrates, in schematic front view, one embodiment of a control module 602 suitable for use in an implantable medical device, such as an electrical stimulation system. The control module 602 includes a connector assembly 644 coupled to an electronic subassembly 610, and a multi-layer covering 640 disposed over the connector assembly 644 and the electronic subassembly 610.

The connector assembly 644 defines at least one port into which a proximal end of an elongated device can be inserted. In FIG. 6, the connector assembly 644 is shown having two ports 604a and 604b. The connector assembly 644 can define any suitable number of ports including, for example, one, two, three, four, five, six, seven, eight, or more ports.

The connector assembly 644 also includes connector contacts, such as connector contact 614, disposed within each port 604a and 604b. When one or more elongated devices is inserted into one (or both) of the ports 604a and 604b, the connector contacts 614 can be aligned with a plurality of terminals disposed along the proximal end(s) of the elongated device(s) to electrically couple the control module 602 to electrodes disposed along the inserted elongated device(s).

In at least some embodiments, the connector assembly 644 is coupled directly to the electronic subassembly 610. In at least some embodiments, the connector contacts 614 of the connector assembly 644 are coupled directly to the electronic subassembly 610. Optionally, the connector assembly 644 may include one or more contact conductors, such as contact conductor 628, coupled to the connector contacts 614. In at least some embodiments, the contact conductors 628 of the connector assembly 644 are coupled to the electronic subassembly 610. It will be understood that when the connector assembly 644 is coupled directly to the electronic subassembly 610 there are no intervening feedthroughs disposed between the connector assembly 644 and the electronic subassembly 610.

In at least some embodiments, the electronic subassembly 610 includes one or more electronic components (see e.g., FIG. 5) disposed on a printed circuit assembly ("PCBA") 622, or similar carrier. The electronic subassembly 610 may include one or more connectors, such as PCBA connector 632, for receiving one or more electrical components, such as the connector assembly 644, an optional power source 620, an optional return electrode 664, or the like. In at least some embodiments, at least one of the connectors is a ground 632a. The connectors can be formed as any suitable type of conductive elements, such pins.

The connector assembly 644 and the electronic subassembly 610 are collectively referred to as a control-module assembly 652. It will be understood that the control-module assembly 652 may include additional elements. For example, the control-module assembly 652 may, optionally, include the power source 620 coupled to the electronic subassembly 610.

In at least some embodiments, the connector assembly 644 couples directly to the electronic subassembly 610 via one or more of the connectors 632. In some embodiments, the contact conductors 628 of the connector assembly 644 are coupled directly to the electronic subassembly 610, via one or more of the connectors 632. In other embodiments, the connector contacts 614 of the connector assembly 644 are coupled directly to the electronic subassembly 610, via one or more of the connectors 632.

The covering 640 may be conformably disposed over the control-module assembly 652. An inner surface of the covering 640 may be in intimate contact with the control-module assembly 652. An inner surface of the covering 640 may directly contact the control-module assembly 652. The covering 640 may encapsulate the control-module assembly 652.

In at least some embodiments, one or more layers of the covering 640 are formed from one or more non-conductive materials. In at least some embodiments, one or more layers of the covering 640 are formed from one or more polymers. The one or more polymer layers of the covering 640 may comprise, consist of, or consist essentially of polymer. In at least some embodiments, the one or more polymer layers are formed from one or more synthetic polymers.

In at least some embodiments, the one or more polymer layers of the covering 640 include epoxy. In embodiments of the covering where the one or more polymer layers of the covering 640 include epoxy, the covering 640 may comprise, consist of, or consist essentially of epoxy. In embodiments of the covering where the one or more polymer layers of the covering 640 include epoxy, the covering 640 may be formed from no less than 50%, 60%, 70%, 80%, 90%, 95%, 96%, 97%, 98%, 99%, or 100% epoxy. Other synthetic polymers may be used in addition to, or in lieu of epoxy including, for example, polyetheretherketone, polyolefin, polyurethane, polyesters, phenolic resins, polytetrafluoroethylene, polyethylene, polypropylene, or the like or combinations thereof.

Optionally, the covering 640 may include one or more additives including, for example, antioxidizers, antimicrobials, dyes, or the like or combinations thereof. In at least some embodiments, the one or more additives are mixed into the one or more polymer layers of the covering 640. The covering 640 may be formed from a biocompatible material. Alternately, the outer surface 642 of the covering 640 may be formed from one or more layers of one or more biocompatible materials. In at least some embodiments, the outer surface 642 of the covering 640 is coated with one or more layers of one or more materials that are harder than the material(s) of the one or more polymer layers.

In at least some embodiments, the covering 640 includes one or more additional layers including, for example, one or more moisture barriers, one or layers of radiopaque coating disposed over the electronic subassembly, one or more layers of metallic coating disposed over the electronic subassembly. Each of these layers is discussed below, with reference to FIGS. 8-9. In at least some embodiments, the one or more moisture barriers are disposed beneath the one or more polymer layers. In at least some embodiments, the one or more layers of radiopaque coating are disposed beneath the one or more polymer layers. In at least some embodiments, the one or more layers of metallic coating are disposed beneath the one or more polymer layers.

The optional return electrode 664 is disposed along the outer surface 642 of the covering 640 and is coupled to the ground 632a. The return electrode 664 may be coupled to the ground 632a via a ground conductor 666. The return electrode 664 may be formed as any suitable conductive element. In at least some embodiments, the return electrode 664 is bonded to the outer surface 642 of the covering 640. The return electrode 664 can be disposed along any suitable portion(s) of the outer surface of the covering 640. In at least some embodiments, the return electrode 664 is flush with the outer surface 642 of the covering 640. In at least some embodiments, the return electrode is disposed in one or more inset regions formed along the outer surface 642 of the covering 640.

In at least some embodiments, the return electrode 664 is formed from a band wrapping around at least one quarter, one half, or three quarters of a perimeter of the covering 640. In at least some embodiments, the return electrode 664 is disposed over no more than 50%, 40%, 30%, 20%, 10%, 5%, of the surface area of the control module 602.

Figure 7B:
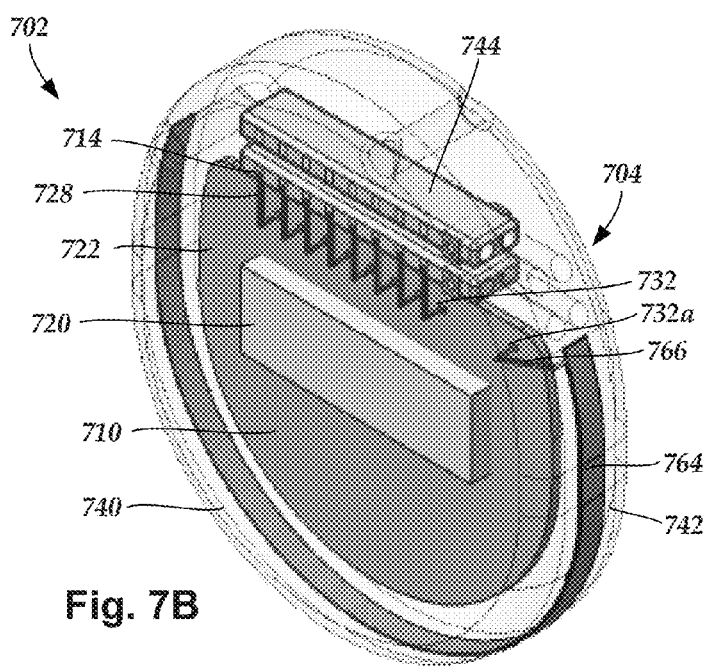
FIG. 7B is a schematic perspective view of another embodiment of a covering disposed over a control module, the control module including a return electrode disposed along an outer surface of the covering, according to the invention.
Figure 7A:
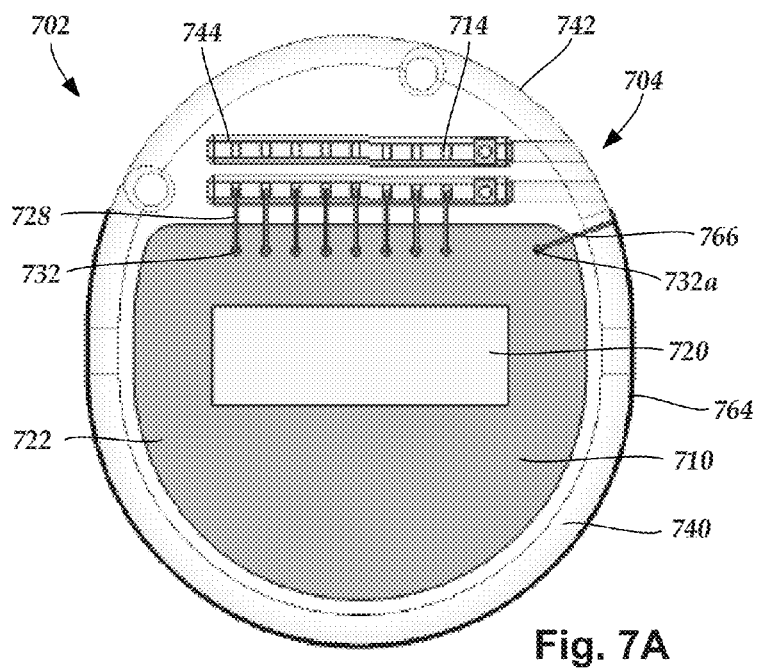
FIG. 7A is a schematic front view of another embodiment of a covering disposed over a control module, the control module including a return electrode disposed along an outer surface of the covering, according to the invention.

FIG. 7A illustrates, in schematic front view, another embodiment of a control module 702 suitable for use in an implantable medical device, such as an electrical stimulation system. FIG. 7B illustrates the control module 702 in schematic perspective view. The control module 702 includes a connector assembly 744 and a power source 720 each coupled to an electronic subassembly 710. A multi-layer covering 740 disposed over each of the connector assembly 744, the electronic subassembly 710, and the power source 720. In FIGS. 7A-7B, the covering 740 is shown as being transparent, for clarity of illustration.

In FIGS. 7A-7B, the connector assembly 744 is shown coupled to the electronic subassembly via contact conductors, such as contact conductor 728, coupled to the connector contacts 714. The connector assembly 744 defines four ports 704. The connector assembly 744 also includes connector contacts, such as connector contact 714, that are disposed within each port 704 and that can be aligned with terminals disposed along proximal end portions of one or more elongated devices to electrically couple the control module 702 to electrodes disposed along the inserted elongated device(s).

In at least some embodiments, the electronic subassembly 710 includes one or more electronic components (see e.g., FIG. 5) disposed on a PCBA 722. The electronic subassembly 710 includes connectors, such as PCBA connectors 732, for receiving the contact conductors 728. The electronic subassembly 710 also includes a ground 732a, for receiving a return electrode 764. Additional connectors are shown in FIGS. 7A-7B coupling the power source 720 to the electronic components.

The return electrode 764 is disposed along an outer surface 742 of the covering 740 and is coupled to the ground 732a via a ground conductor 766. In FIGS. 7A-7B, the return electrode 764 is shown formed from a band wrapped around at least half of a circumference of the covering 740.

Figure 8:
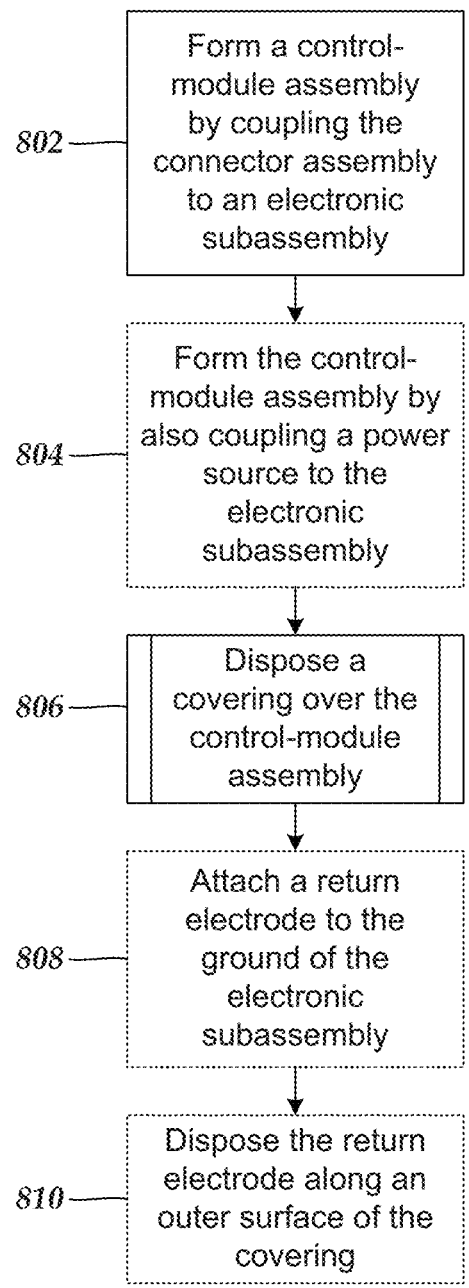
FIG. 8 is a flow diagram illustrating one embodiment of steps for forming a control module that includes disposing a covering over a control-module assembly of the control module, according to the invention.

FIG. 8 illustrates one embodiment of a technique for fabricating the control module. In step 802, a control-module assembly is formed by coupling the connector assembly to the electronic subassembly. Optionally, in step 804, formation of the control-module assembly further includes coupling a power source to the electronic subassembly. In step 806, a covering is disposed over the control-module assembly. Optionally, in step 808, a return electrode is attached to the ground of the electronic subassembly. Optionally, in step 810, the return electrode is disposed along an outer surface of the covering.

The return electrode can be attached to the ground of the electronic subassembly (as described in step 808) either directly or via the ground conductor. In at least some embodiments, the covering is disposed over the control-module assembly with the ground conductor extending at least partially through the covering. In which case, the return electrode can be coupled to the ground conductor and disposed along the outer surface of the covering after the housing is at least partially hardened.

The return electrode can be disposed along the outer surface of the covering (as described in step 810) using any suitable technique including, for example, bonding the return electrode to the outer surface of the covering, or casting the return electrode into an outer portion of the covering.

Figure 9:
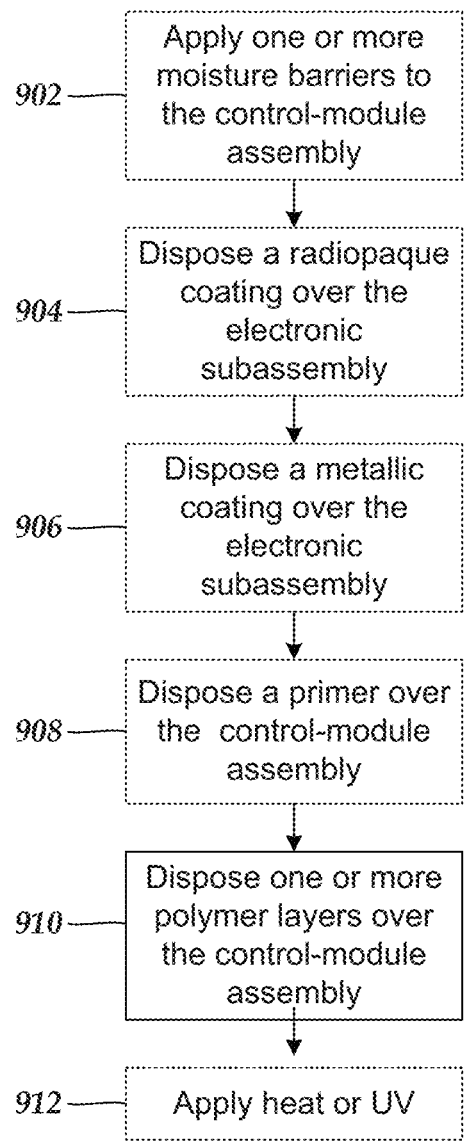
FIG. 9 is a flow diagram illustrating one embodiment of steps for disposing a covering over a control-module assembly of a control module, according to the invention.

FIG. 9 illustrates one embodiment of disposing a covering over the control-module assembly (step 806). Optionally, in step 902, one or more moisture barriers are applied to one or more components of the control-module assembly. Optionally, in step 904, a radiopaque coating is disposed over one or more portions of the electronic subassembly. Optionally, in step 906, a metallic coating is disposed over one or more portions of the electronic subassembly. Optionally, in step 908, a primer is disposed over the control-module assembly. In step 910, one or more polymer layers are disposed over the control-module assembly. Optionally, in step 912, heat, or ultraviolet radiation, or both, is applied to the control-module assembly to promote curing of one or more layers of the covering.

Any suitable moisture barrier may be applied to the control-module assembly, or to one or more components (e.g., the electronic subassembly or portions thereof) of the control-module assembly (as described in step 902) including, for example, parylene. In at least some embodiments, the control-module assembly, or one or more components (e.g., the electronic subassembly or portions thereof) of the control-module assembly, are pre-cleaned prior to applying one or more of the moisture barriers. In at least some embodiments, pre-cleaning involves using one or more heat treatments, vacuum treatments, plasma treatments, or the like or combinations thereof. It will be understood that, during application of one or more of the moisture barriers, the connector contacts of the connector assembly may be protected from direct exposure to the moisture barrier using one or more suitable masking elements, such as one or more port plugs.

It may be advantageous to apply the radiopaque coating to the electronic subassembly (as described in step 904) to protect against potential unwanted discovery by third parties of the electronic design of the electronic subassembly. The radiopaque coating may function as a shield to prevent use of x-ray imaging to image the encapsulated electronics.

It may be advantageous to apply a metallic coating (e.g., tungsten, or the like) over one or portions of the electronics of the electronic subassembly (as described in step 906) to protect the electronics of the electronic subassembly from undesirable heating during exposure to RF irradiation (e.g., during a magnetic resonance imaging procedure).

It may be advantageous to apply a primer to the control-module assembly prior to disposing one or more polymer layers over the control-module assembly (as described in step 908) to facilitate adhesion of the polymer to the control-module assembly.

The one or more layers of polymer can be disposed over the control-module assembly (as described in step 910) using any suitable technique. In at least some embodiments, the control-module assembly is cast in a mold. In at least some embodiments, the control-module assembly is cast using a single mold. It will be understood that disposing one or more layers of polymer over the control-module assembly, and eliminating the sealed metallic case around the electronic subassembly and the corresponding feedthroughs enables the control module to be formed in a wide variety of shapes and sizes.

It may be advantageous to facilitate curing of one or more layers of the covering disposed over the control-module assembly (as described in step 912). Facilitation of curing may involve application of heat, ultraviolet radiation, or the like or combinations thereof.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A control module for an electrical stimulation system, the control module comprising:
    an electronic subassembly;
    a connector assembly coupled to the electronic subassembly, the connector assembly defining a port configured and arranged for receiving a proximal end portion of an electrical stimulation lead, the connector assembly comprising a plurality of connector contacts coupled to the electronic subassembly and open to the port, the plurality of connector contacts configured and arranged to couple to a plurality of terminals disposed along the proximal end portion of the electrical stimulation lead when the electrical stimulation lead is received by the port; and
    a covering conformably disposed over the electronic subassembly and the connector assembly, the covering having an inner surface, an outer surface, and a plurality of layers, wherein at least one of the plurality of layers is a polymer layer and at least another one of the plurality of layers is a radiopaque layer, and wherein the radiopaque layer is disposed beneath the polymer layer.

2. The control module of claim 1, wherein the connector assembly further comprises a plurality of connector conductors coupled to the plurality of connector contacts, the plurality of connector conductors coupled directly to the electronic subassembly.

3. The control module of claim 1, further comprising a power source disposed in the control module and coupled to the electronic subassembly, wherein the covering is disposed over the power source.

4. The control module of claim 1, further comprising a return electrode disposed along a portion of the outer surface of the covering, the return electrode coupled electrically to the electronic subassembly.

5. The control module of claim 1, further comprising at least one moisture barrier disposed beneath the polymer layer.

6. The control module of claim 1, further comprising a metallic coating disposed over the electronic subassembly and disposed beneath the polymer layer.

7. An implantable electrical stimulation system comprising:
    the control module of claim 1; and
    at least one lead configured and arranged for insertion into the connector assembly of the control module, the at least one lead comprising
        at least one lead body having a distal end portion, a proximal end portion, and a longitudinal length;
        a plurality of electrodes disposed along the distal end portion of the at least one lead body;
        a plurality of terminals disposed along the proximal end portion of the at least one lead body; and
        a plurality of conductors electrically coupling the plurality of terminals to the plurality of electrodes.

8. A method of forming a control module of an implantable medical device, the method comprising:
    forming a control-module assembly by coupling a connector assembly to an electronic subassembly; and
    conformably disposing a covering over the control-module assembly, the covering comprising a plurality of layers, wherein at least one of the plurality of layers is a polymer layer and at least another one of the plurality of layers is a radiopaque layer, and wherein the radiopaque layer is disposed beneath the polymer layer.

9. The method of claim 8, wherein conformably disposing a covering over the control-module assembly comprises applying a moisture barrier beneath the polymer layer.

10. The method of claim 8, wherein conformably disposing a covering over the control-module assembly comprises disposing a metallic coating beneath the polymer layer to reduce heating during exposure of the control module to RF irradiation.

11. The method of claim 8, further comprising
disposing a return electrode along an outer surface of the covering; and
coupling the return electrode to the electronic subassembly.

12. A control module for an electrical stimulation system, the control module comprising:
an electronic subassembly;
a connector assembly coupled to the electronic subassembly, the connector assembly defining a port configured and arranged for receiving a proximal end portion of an electrical stimulation lead, the connector assembly comprising a plurality of connector contacts coupled to the electronic subassembly and open to the port, the plurality of connector contacts configured and arranged to couple to a plurality of terminals disposed along the proximal end portion of the electrical stimulation lead when the electrical stimulation lead is received by the port; and
a covering conformably disposed over the electronic subassembly and the connector assembly, the covering having an inner surface, an outer surface, and a plurality of layers, wherein at least one of the plurality of layers is a polymer layer and at least another one of the plurality of layers is a metallic layer, and wherein the metallic layer is disposed beneath the polymer layer.

13. The control module of claim 12, further comprising a return electrode disposed along a portion of the outer surface of the covering, the return electrode coupled electrically to the electronic subassembly.

14. The control module of claim 12, further comprising a moisture barrier disposed beneath the polymer layer.

15. The control module of claim 12, further comprising a radiopaque coating disposed beneath the polymer layer.

16. An implantable electrical stimulation system comprising:
the control module of claim 12; and
at least one lead configured and arranged for insertion into the connector assembly of the control module, the at least one lead comprising
at least one lead body having a distal end portion, a proximal end portion, and a longitudinal length;
a plurality of electrodes disposed along the distal end portion of the at least one lead body;
a plurality of terminals disposed along the proximal end portion of the at least one lead body; and
a plurality of conductors electrically coupling the plurality of terminals to the plurality of electrodes.

17. A method of making an implantable medical device, the method comprising:
forming a control-module assembly by coupling the connector assembly of claim 12 to an electronic subassembly; and
conformably disposing a covering over the control-module assembly, the covering comprising a plurality of layers, wherein at least one of the plurality of layers is a polymer layer and at least another one of the plurality of layers is a metallic layer, and wherein the metallic. layer is disposed beneath the polymer layer.

18. The method of claim 17, wherein conformably disposing the covering over the control-module assembly includes conformably disposing a moisture barrier layer beneath the polymer layer.

19. The method of claim 17, wherein conformably disposing the covering over the control-module assembly includes conformably disposing a radiopaque layer beneath the polymer layer.

* * * * *